US012778806B2

(12) United States Patent
McCain et al.

(10) Patent No.: US 12,778,806 B2
(45) Date of Patent: Nov. 3, 2026

(54) MULTILAYER GARMENTS WORN DURING WOUND CARE

(71) Applicant: Create To Overcome LLC, Pittsburg, CA (US)

(72) Inventors: Aisha Michelle McCain, Pittsburg, CA (US); Annemarie Noelle Sheets, Pittsburg, CA (US)

(73) Assignee: CREATE TO OVERCOME LLC, Pittsburg, CA (US)

( * ) Notice: Subject to any disclaimer, the term of this patent is extended or adjusted under 35 U.S.C. 154(b) by 0 days.

(21) Appl. No.: 18/967,504

(22) Filed: Dec. 3, 2024

(65) Prior Publication Data

US 2025/0169993 A1 May 29, 2025

Related U.S. Application Data

(63) Continuation-in-part of application No. 16/948,466, filed on Sep. 20, 2020, now Pat. No. 12,156,558.

(60) Provisional application No. 62/903,612, filed on Sep. 20, 2019.

(51) Int. Cl.
*A61F 13/00* (2024.01)
*A61F 13/01* (2024.01)

(52) U.S. Cl.
CPC .. *A61F 13/00059* (2013.01); *A61F 13/01029* (2024.01); *A61F 13/01042* (2024.01); *A61F 2013/00157* (2013.01); *A61F 2013/0028* (2013.01)

(58) Field of Classification Search
None
See application file for complete search history.

(56) References Cited

U.S. PATENT DOCUMENTS

| | | | | |
|---|---|---|---|---|
| 7,329,232 B2 * | 2/2008 | Lipshaw | A61F 13/06 602/61 |
| 9,125,727 B2 * | 9/2015 | Dallafior | A61F 13/01038 |
| 10,603,220 B2 * | 3/2020 | Ahmed | A61F 13/01046 |
| 12,279,886 B1 * | 4/2025 | Chavez | A61B 5/6804 |

OTHER PUBLICATIONS

Drake, Nadia, Opal-Inspired Material Changes Color When Stretched, Wired, Jun. 4, 2013 https://wired.com/2013/06/new-color-changing-material. (Year: 2013).*

Dhar, Payal, Simple method creates stretchy color changing films, Chemicals and Engineering News Aug. 2022 https://cen.acs.org/materials/photonics/Simple-method-creates-stretchy-color/100/web/2022/08 (Year: 2022).*

* cited by examiner

*Primary Examiner* — Kim M Lewis
(74) *Attorney, Agent, or Firm* — Cynthia S. Lamon; Lamon Patent Services

(57) ABSTRACT

A wound recovery garment includes a multilayer fabric. The multilayer fabric comprises at least first layer including opalescent microparticles, a second layer for absorbing and holding moisture, and a third layer adjacent to tissue or a wound enabled to absorb moisture and provide microsensor beads to an immediate area to detect a state of the tissue or wound. The first layer is formed from compressive, elastic material that supplies compression forces to tissue. The first layer is an elastic exterior layer incorporating the opalescent microparticles and is visible to outside viewers. The microparticles change color according to a stretch factor of the first layer indicating a pressure reading to the viewer.

19 Claims, 9 Drawing Sheets

MULTILAYER GARMENTS WORN DURING WOUND CARE

CROSS REFERENCE TO RELATED APPLICATIONS

This application is a Continuation-in-Part of U.S. application Ser. No. 16/948,466, which claims the benefit under 35 U.S.C. § 119 from U.S. Provisional Patent Application Ser. No. 62/903,612, entitled "Multilayer Garments Worn During Wound Care," filed on Sep. 20, 2019, the subject matter of which is incorporated herein by reference.

TECHNICAL FIELD

The present invention relates generally to garments and clothing. Specifically, incorporating smart materials into forming garments to cover and treat damaged human/animal tissue.

SUMMARY

A wound recovery garment includes a multilayer fabric. The multilayer fabric comprises a first layer, a second layer, and a third layer. The multilayer fabric draws moisture from the skin tissues, including wounded or burned tissue recovering from trauma. The third layer removes moisture from wounded tissue without sticking to skin. The first layer is formed from compressive, elastic material that supplies compression forces to wounded tissue. The second layer is an absorbent layer that receives the moisture from the third layer and stores tissue moisture in a sponge-like fashion. The second layer is disposed between the first layer and the third layer. The first layer is an exterior layer and is visible to outside viewers. No body fluid or blood leaks through the first layer. Individuals recovering from trauma are able to comfortably go outside without being concerned with body fluids soaking through and being visible to others.

The foregoing is a summary and thus contains, by necessity, simplifications, generalizations and omissions of detail; consequently it is appreciated that the summary is illustrative only. Still other methods, and structures and details are set forth in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Figure 1:
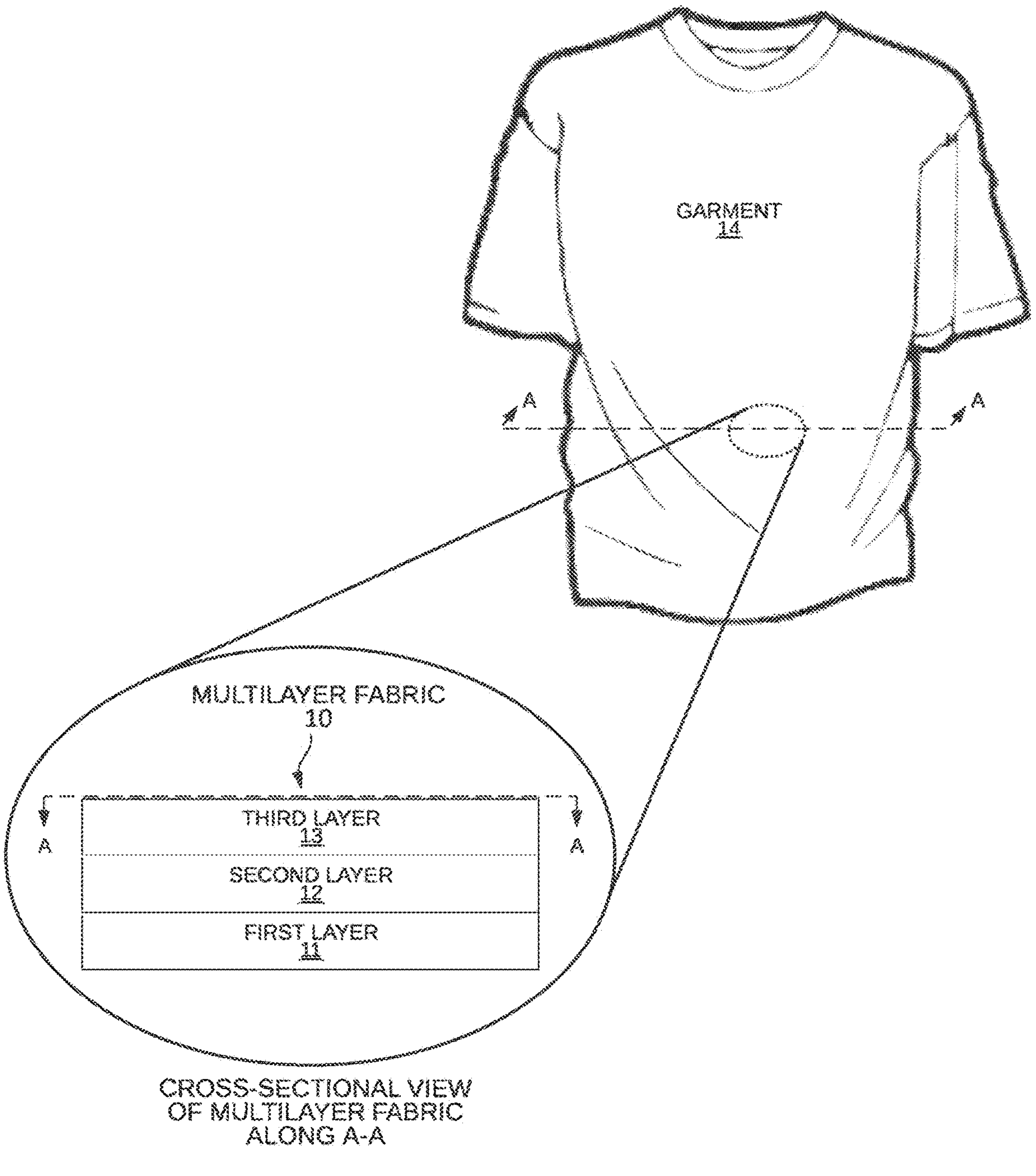
FIG. 1 a diagram of a cross-sectional view of multilayer fabric 10.

Reference will now be made in detail to background examples and some embodiments of the invention, examples of which are illustrated in the accompanying drawings. FIG. 1 a diagram of a cross-sectional view of multilayer fabric 10. The multilayer fabric 10 comprises a first layer 11, a second layer 12, and a third layer 13. The multilayer fabric 10 is part of a garment 14. In one embodiment, the multilayer fabric 10 extends throughout the entirety of the garment 14. In another embodiment, only parts of the garment 14 have the multilayer fabric 10.

The multilayer fabric 10 draws moisture from the skin tissues, including wounded or burned tissue recovering from trauma. The first layer 11 has a tissue contact surface that is identified by reference numeral 19 in FIG. 3. The first layer 11 draws moisture away from wounded tissue and transfers the moisture into the second layer 12. The second layer 12 is an absorbent layer and receives and stores tissue moisture received via the first layer 11. The second layer 12 is disposed between the first layer 11 and the third layer 13. The third layer 13 is an exterior layer. The third layer 13 has an external environment contact surface and is visible to an outer environment.

The garment 14 is any garment that can be worn against skin. As depicted in FIG. 1, the garment is a shirt with short sleeves, otherwise known in the art as a T-shirt. The garment 14 assists with individuals recovering from wounds or burns to heal. The garment 14 allows wounds or damaged tissue to breathe and heal without moisture. The garment 14 does not stick to wounds and absorbs body fluid or blood without leaking thru to outer layers. The garment 14 permits individuals with wounds to go outside in public without feeling self-conscious or embarrassed. In the case of conventional garments, body fluids tend to leak through conventional garments. On the other hand, the novel garments 14 with the multilayer fabric 10 prevents body fluids and blood from leaking through and being visible to external environments.

Figure 2:
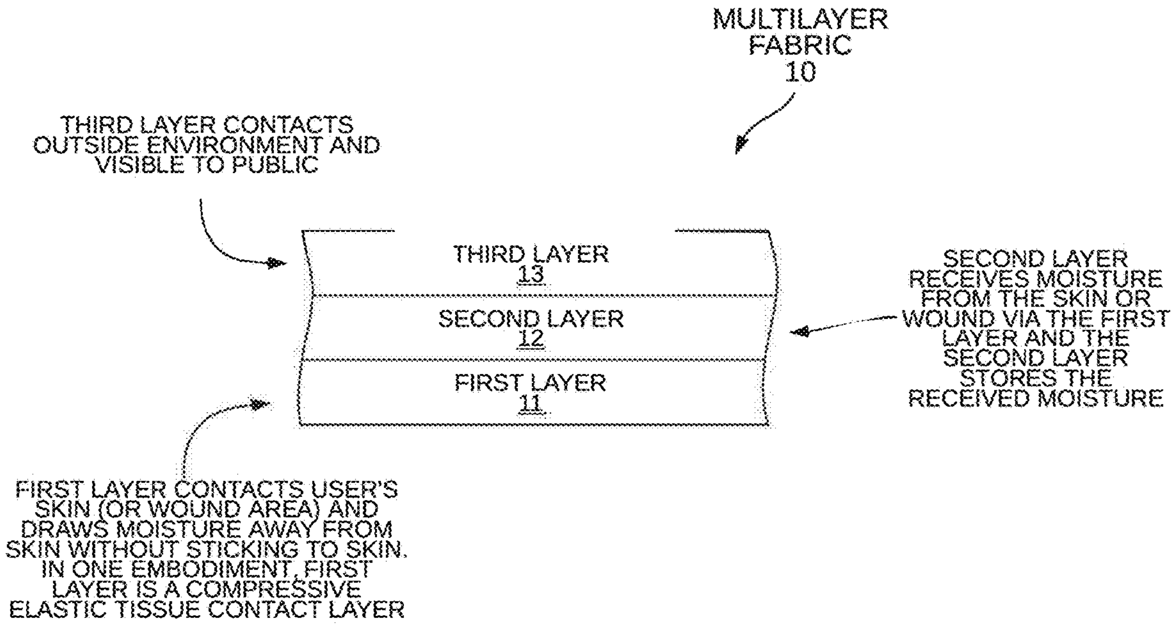
FIG. 2 a diagram of a cross-sectional view of multilayer fabric 10 showing the various layers of fabric 10.

FIG. 2 a diagram of a cross-sectional view of multilayer fabric 10 showing the various layers of fabric 10. A first surface of the second layer 12 contacts a surface of the first layer 11. A second surface of the second layer 12 contacts a surface of the third layer 13. In one embodiment, the layers are mechanically attached together through a stitching process. In another embodiment, the layers are adhesively attached together through an adhesion process.

The first layer 11 is a smooth fabric material that is cool to touch and does not stick to wounded tissue or skin. The first layer 11 wicks moisture away from wounded tissue or skin into the interior second layer 12. In one embodiment, the first layer 11 is formed from a poly and spandex material. For example, the first layer 11 is formed from 90% poly material and 10% spandex material. In another embodiment, the first layer 11 is formed from a poly Lycra tricot fabric. For example, the first layer 11 is formed from 73% poly material and 27% lycra material.

The second layer 12 holds and collects the moisture from wounded tissue or skin. The second layer 12 is an absorbent layer of fabric. The second layer 12 operates as a sponge to absorb the moisture received onto the first layer 11 from the skin. In one embodiment, the second layer 12 is formed from cotton fibers. For example, the second layer 12 is formed from a 3D Cotton Dimple. In another embodiment, the second layer 12 is formed from bamboo fibers. For example, the second layer 12 is formed from a Bamboo Lining Fleece.

The third layer 13 is an outer garment layer. The third layer 13 is viewed as a regular garment to outside viewers. The first layer 11 and the second layer 12 are not visible from the outside. The first layer 11 and the second layer 12 prevent body fluid or blood from leaking through to the third layer 13. In one embodiment, the third layer 13 is formed from a woven fabric. In another embodiment, the third layer 13 is formed from a knit fabric.

Figure 3:
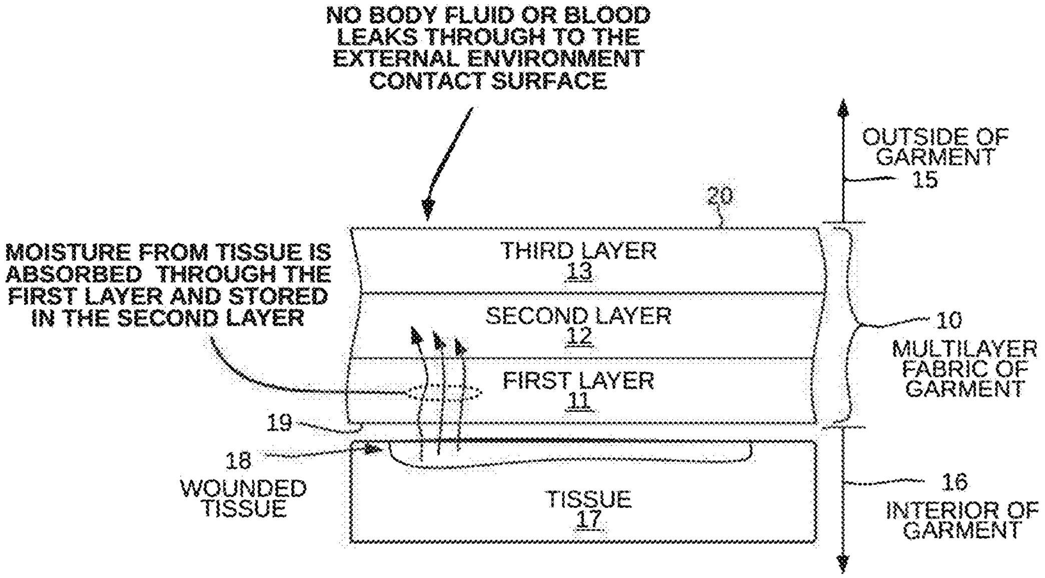
FIG. 3 is a diagram of a cross-sectional view of multilayer fabric 10 showing how moisture is absorbed and stored within the fabric 10.

FIG. 3 is a diagram of a cross-sectional view of multilayer fabric 10 showing how moisture is absorbed and stored within the fabric 10. The first layer 11 is disposed adjacent to the tissue of the wearer 17. The third layer 13 is exposed to an outside environment 15. The third layer 13 has an external environment contact surface 20. The first layer 11 has a tissue contact surface 19. The tissue contact surface 19 is disposed within an interior 16 of the garment 14. Part or all of the tissue 17 may contact the first layer 11. The tissue 17 optionally has a wounded or burn area 18 that is recovering from trauma. In operation, the moisture from the tissue 17 and wound 18 is absorbed through the first layer 11 and stored in the second layer 12. No body fluid or blood leaks through to the external environment contact surface 20.

Figure 4:
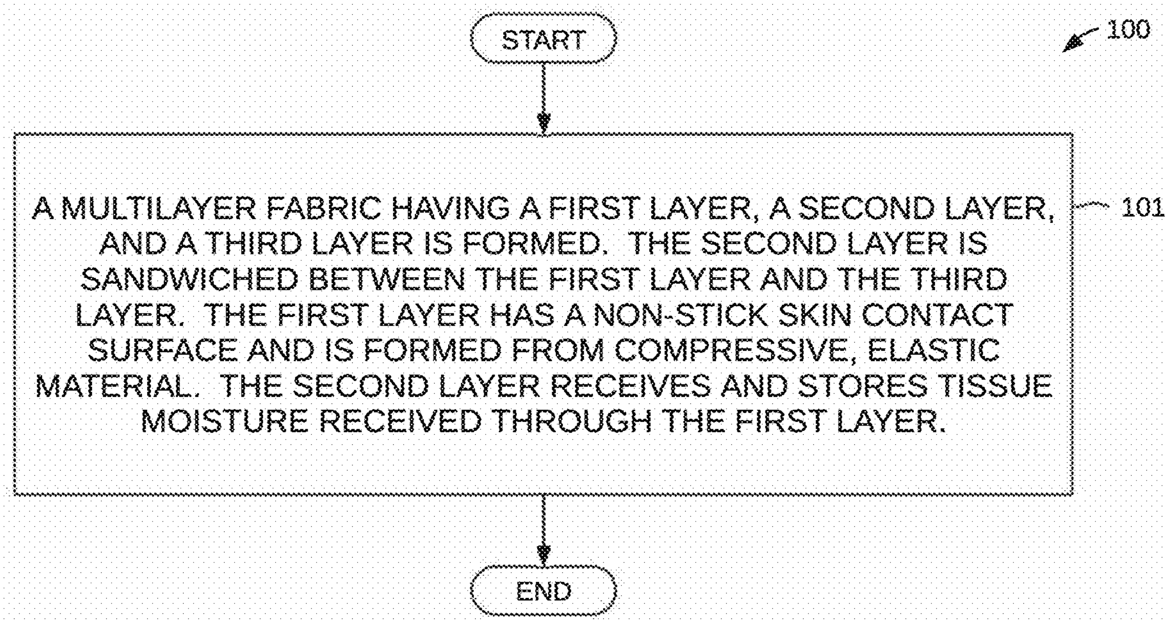
FIG. 4 is a diagram of a flowchart 100 of a method in accordance with another novel aspect.

FIG. 4 is a diagram of a flowchart 100 of a method in accordance with another novel aspect. In a first step (101), a multilayer fabric having a first layer, a second layer, and a third layer is formed. The second layer is sandwiched between the first layer and the third layer. The first layer has a non-stick skin contact surface and is formed from compressive, elastic material. The second layer receives and stores tissue moisture received through the first layer.

Figure 5:
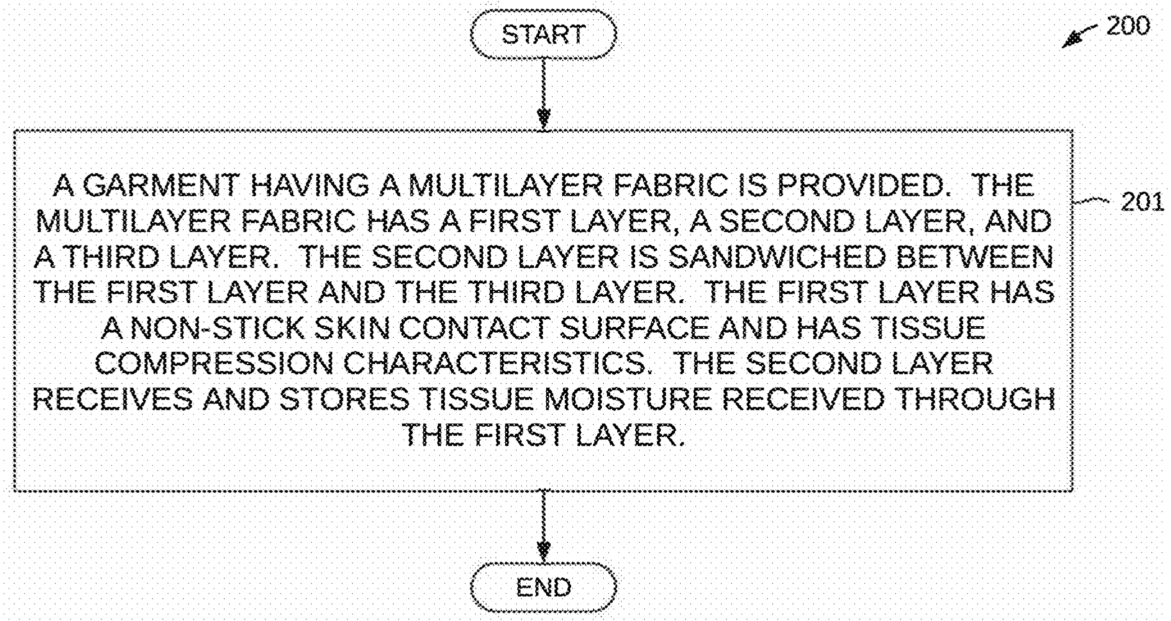
FIG. 5 is a diagram of a flowchart 200 of a method in accordance with another novel aspect.

FIG. 5 is a diagram of a flowchart 200 of a method in accordance with another novel aspect. In a first step (201), a garment having a multilayer fabric is provided. The multilayer fabric has a first layer, a second layer, and a third layer. The second layer is sandwiched between the first layer and the third layer. The first layer has a non-stick skin contact surface and has tissue compression characteristics. The second layer receives and stores tissue moisture received through the first layer.

Figure 6:
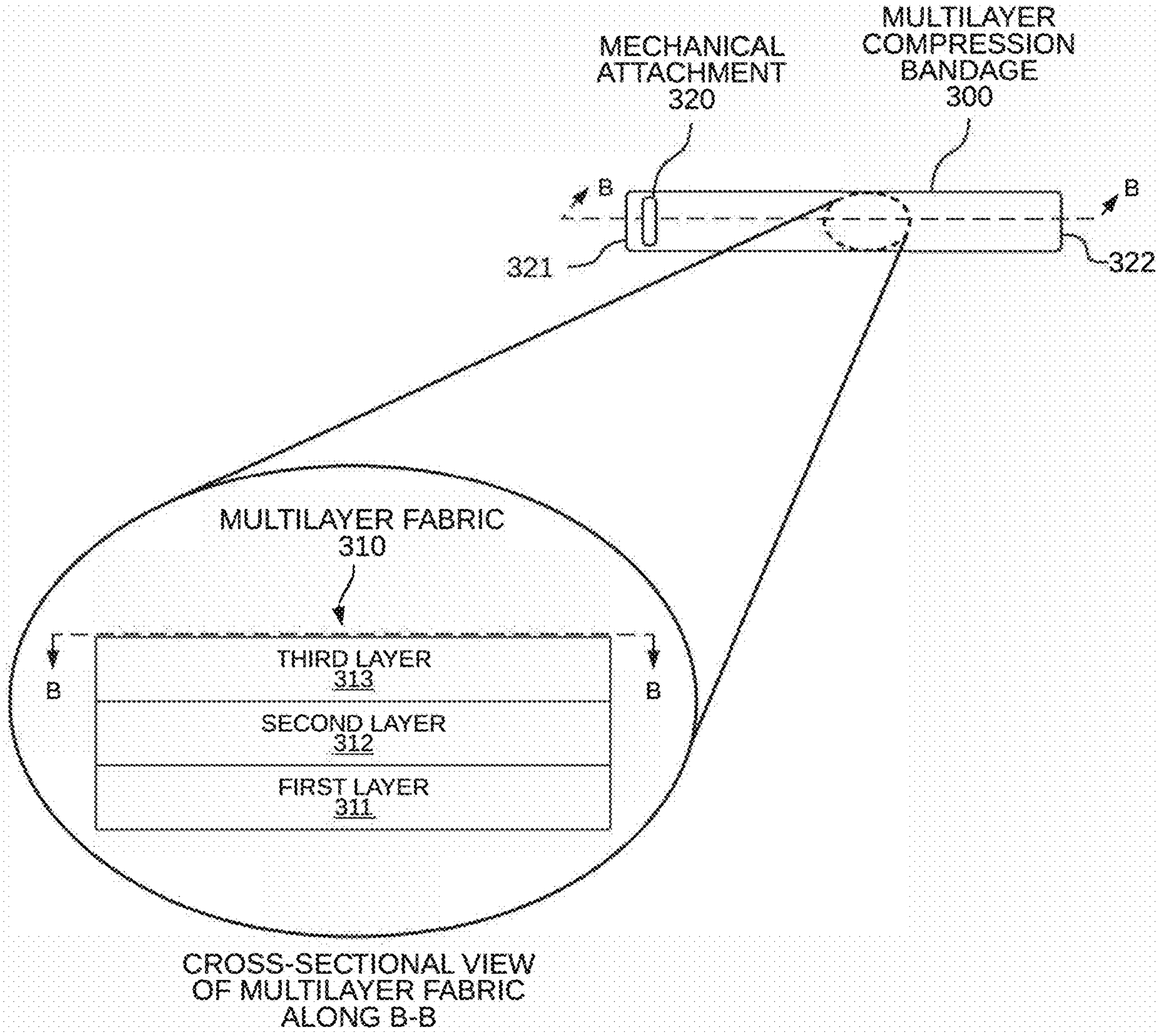
FIG. 6 is a diagram of a multilayer compression bandage 300 in accordance with one embodiment.

FIG. 6 is a diagram of a multilayer compression bandage 300 in accordance with one embodiment. The multilayer compression bandage 300 comprises a multilayer fabric 310 having at least three layers, at least one mechanical attachment 320, a first end 321, and a second end 322. The multilayer fabric 310 includes first layer 311, a second layer 312, and a third layer 313. In one embodiment, the multilayer fabric 310 extends throughout the entirety of the bandage 300. In another embodiment, only parts of the bandage 300 have the multilayer fabric 310.

In operation, the multilayer compression bandage 300 is applied to tissue of a user. The multilayer compression bandage 300 is wrapped around the tissue of the user. The mechanical attachment 320 is used to retain the multilayer compression bandage 300 in place and apply compression to the tissue. After the multilayer compression bandage 300 is wrapped around the tissue and set at a desired location and compression, the mechanical attachment 321 is attached to the multilayer compression bandage 300.

The multilayer fabric 310 draws moisture from the skin tissues, including wounded or burned tissue recovering from trauma. The first layer 311 has a tissue contact surface. The first layer 311 draws moisture away from wounded tissue and transfers the moisture into the second layer 312. The second layer 312 is an absorbent layer and receives and stores tissue moisture received via the first layer 311. The second layer 312 is disposed between the first layer 311 and the third layer 313. The third layer 313 is an exterior layer. The third layer 313 has an external environment contact surface and is visible to an outer environment.

In this example, the multilayer compression bandage 300 shown in FIG. 6 has a rectangular shape. It is appreciated that the multilayer compression bandage 300 is any type of bandage or medical wound covering that can be worn against skin. The multilayer compression bandage 300 assists with individuals recovering from wounds or burns to heal. The multilayer compression bandage 300 allows wounds or damaged tissue to breathe and heal without moisture. The multilayer compression bandage 300 does not stick to wounds and absorbs body fluid or blood without leaking thru to outer layers. The multilayer compression bandage 300 permits individuals with wounds to go outside in public without feeling self-conscious or embarrassed. The multilayer fabric 10 prevents body fluids and blood from leaking through and being visible to external environments and also applies compressive forces to recovering tissue.

The first surface of the second layer 312 contacts a surface of the first layer 311. A second surface of the second layer 312 contacts a surface of the third layer 313. In one embodiment, the layers are mechanically attached together through a stitching process. In another embodiment, the layers are adhesively attached together through an adhesion process.

The first layer 311 is a smooth fabric material that is cool to touch and does not stick to wounded tissue or skin. The first layer 311 wicks moisture away from wounded tissue or skin into the interior second layer 312. In one embodiment, the first layer 311 is formed from a poly and spandex material. For example, the first layer 311 is formed from 90% poly material and 10% spandex material. In another embodiment, the first layer 311 is formed from a poly lycra tricot fabric. For example, the first layer 311 is formed from 73% poly material and 27% lycra material.

The second layer 312 holds and collects the moisture from wounded tissue or skin. The second layer 312 is an absorbent layer of fabric. The second layer 312 operates as sponge to absorb the moisture received onto the first layer 311 from the skin. In one embodiment, the second layer 312 is formed from cotton fibers. For example, the second layer 312 is formed from a 3D Cotton Dimple. In another embodiment, the second layer 312 is formed from bamboo fibers. For example, the second layer 312 is formed from a Bamboo Lining Fleece.

The third layer 313 is an outer layer that contacts the environment. The third layer 313 is selected to be visually appealing and not appear as a medical type of bandage. The first layer 311 and the second layer 312 are not visible from the outside. The first layer 311 and the second layer 312 prevent body fluid or blood from leaking through to the third layer 313. In one embodiment, the third layer 313 is formed from a woven fabric. In another embodiment, the third layer 313 is formed from a knit fabric.

Figure 7:
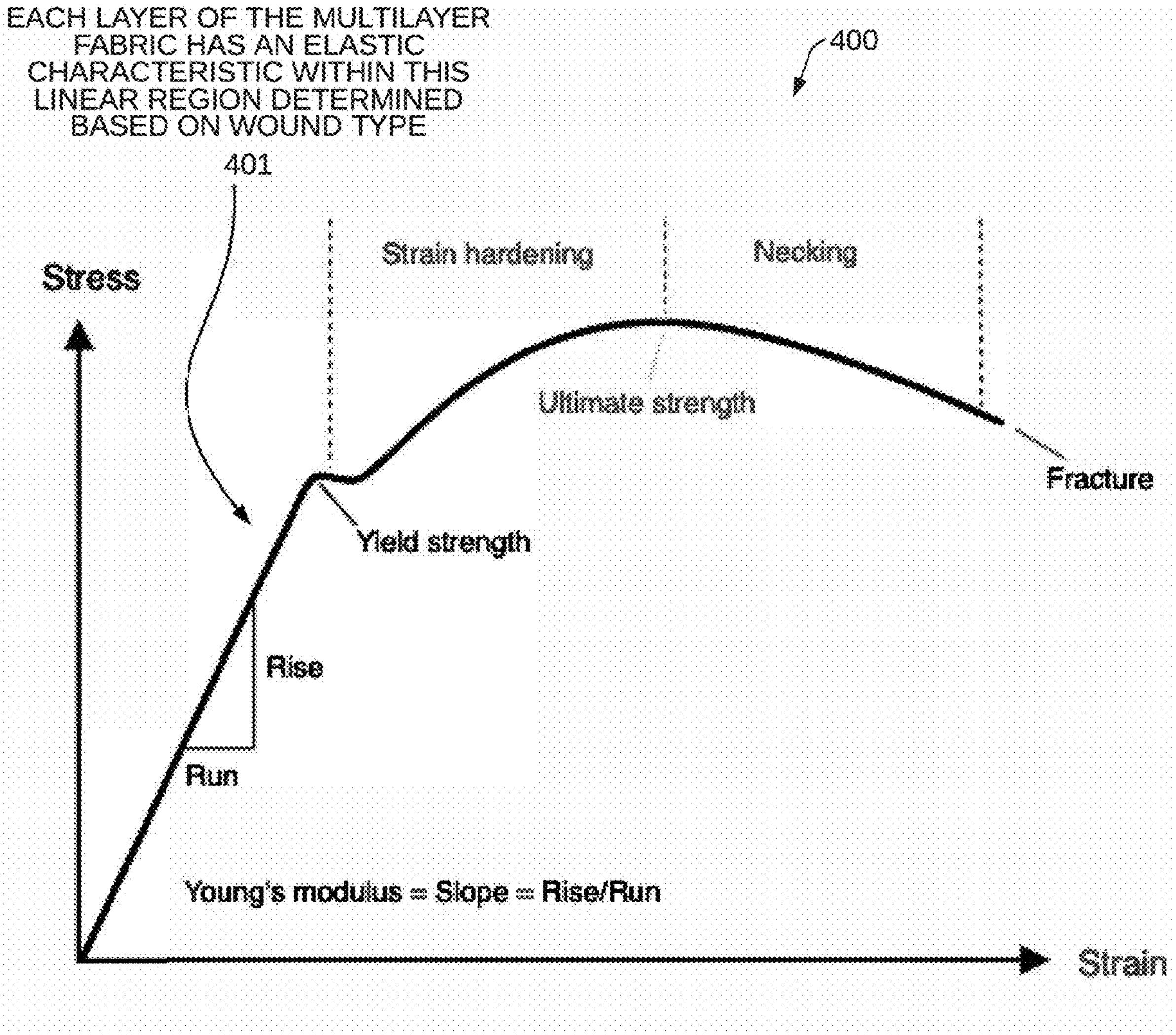
FIG. 7 is a graph 400 showing how selection of material for the multilayer fabrics 10 and 310 having desired elasticity improves wound treatment outcomes.

FIG. 7 is a graph 400 showing how selection of material for the multilayer fabrics 10 and 310 having desired elasticity improves wound treatment outcomes. Reference numeral 401 identifies a linear region. Each layer of the multilayer fabrics 10 and 310 has an elastic characteristic within this linear region determined based on wound type. The layers of the multilayer fabrics 10 and 310 have elastic properties that provide sufficient compression to wounded tissue to protect tissue, avoid further injury, and enhance healing.

Wounds include acute and chronic disruption of the skin or mucous membranes from any cause whether traumatic, environmental, iatrogenic, or due to a medical condition. Wounds are extremely common and often need dressings or bandages, and frequent bandage changes. Bandages are often difficult to change without assistance. Tape and medical adhesives can cause skin damage. Plastic traps moisture against the skin. Dressings often stick painfully to wounds and may cause further damage. Dressings and bandages also tend to fall off with activity.

Elasticity of the multilayer fabric is desirable because it moves with a users's body. A multilayer fabric having elastic qualities is operable to hold dressings in place and provides compression forces on wounded tissue. Compression is desirable to limit or prevent swelling, to provide support to healing wounds, to promote hemostasis, to prevent or treat thrombosis, or to decrease pain. It is appreciated that applying compression forces to wounded tissue provides many additional medical benefits in addition to those presented herein.

Excessive or insufficient compression can be ineffectual or dangerous depending on underlying wound presentation. Conventional bandages typically tend to be difficult to apply, highly variable, very expensive, can lead to further skin damage or allergic reactions, or look characteristically medical ("like a mummy"). Clinical data indicates that medical outcomes are improved and healing hastened when patients recovering from trauma are not perceived as being ill in public settings.

In various embodiments, a multilayer fabric of at least 3 layers is provided as part of a garment or bandage. Each layer of the multilayer fabric has elastic properties specially designed in wrap-around style fashion for application to chest, abdomen, limbs, or other body parts. A first layer, or dressing layer, is applied directly to tissue. A second layer, or absorptive layer, draws and retains drainage from the dressing layer. A third layer, or bandage Layer, supports the other two layers and provides padding and protection from additional injury.

The novel multilayer fabric is usable to treat wounds in connection with sunburn, poison ivy/oak/sumac lymphedema, thrombophlebitis, insect bites, psoriasis, contact dermatitis, dialysis fistula, PICC line, post surgical sprain, strain, or injury, fatigue prevention, DVT, wound dehiscence, hernias, orthostatic hypotension, diabetic wounds, venous stasis wounds, arterial insufficiency, cardiogenic edema, Crohn's Disease, colostomy or ileostomy, urostomy, peritoneal dialysis catheter, pregnancy-related edema, postpartum C-section support, cellulitis, burn injuries, decrease scar formation, friable skin due to extremes of age, herpes zoster, bite or crush injuries, skin cancer, complex regional pain, neuropathic pain, topical medication, varicose veins, protection of pressure points prevent additional injury, and psychosocial improvement performance enhancement research.

In one embodiment, the multilayer fabric includes three and only three layers. The multilayer fabric includes a hook-and-loop fastener or hook-and-pile fastener to attach the multilayer fabric to human tissue.

In another embodiment, the multilayer fabric includes at least three layers. The multilayer fabric includes a hook-and-loop fastener or hook-and-pile fastener (such as VELCRO®) to attach the multilayer fabric to human tissue. An indicator is attached to the multilayer fabric. The indicator provides stretch or pressure feedback indicative of the pressure the multilayer fabric is applying to the wounded tissue. The indicator provides invaluable information for identifying an ideal and medically efficacious amount of compression for individuals with certain underlying conditions that are sensitive to pressure.

In yet another embodiment, the multilayer fabric includes at least three layers. The multilayer fabric includes a hook-and-loop fastener or hook-and-pile fastener (such as VELCRO®) to attach the multilayer fabric to human tissue. A sensor is attached to the multilayer fabric. The sensor provides stretch or pressure feedback indicative of the pressure the multilayer fabric is applying to the wounded tissue. The sensor is usable to apply specific pressure as desired and provides maximum control over desired pressure. This embodiment is useful in research, diagnosis, and adjunctive therapy.

In still yet another embodiment, the multilayer fabric comprises at least three layers. At least one of the layers includes a medicated dressing layer. At least another of the layers includes a printed flexible circuit structure having an array of sensors and an element taken from the group consisting of a heating element that supplies heat to wounded tissue, a vibrating element that supplies vibration to wounded tissue, an electrical stimulation element that provides electrical stimulation to the wounded tissue, and a treatment modality element consistent with another treatment modality.

In additional embodiments the multi-layer fabric may be a smart fabric having modifications suited to treatment of not only wounds, but also conditions such as, but not limited to, psoriasis, eczema, blistering disorders, autoimmune diseases like lupus, and conditions like diabetes and Crohn's disease, where temperature and pressure may be monitored and applied around the abdomen, for example. Additionally, the multilayer fabric may be used for prevention of deep vein thrombosis and burn care at various stages of healing.

One aspect of healing human and animal tissue is what pressure (PSI) is the bandage applying to the tissue. There is a challenge in creating a body-worn smart fabric that can accurately measure pressure on tissue adjacent to the smart fabric based on stretch of that fabric. In these cases, the smart fabric is typically worn around a limb or other extremity, around a chest or abdomen, for example, where the smart fabric creates a closed loop. A smart fabric known to this inventor includes an opalescence technology which includes an ability to distribute a concentration of opalescent beads and bead fragments on a stretch fabric.

Figure 8A:
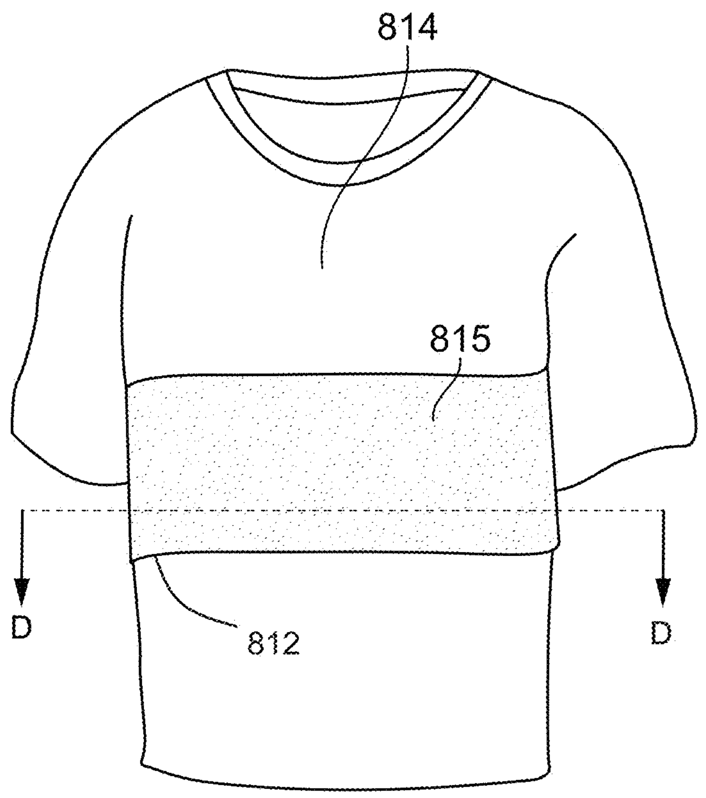
FIG. 8A is an embodiment showing a smart fabric formed on a garment.

FIG. 8A shows an example of the smart fabric having opalescent technology. Many types of wounds and tissue disease, either internal or external, benefit from treatments with bandages applying a specific pressure or a pressure range. For example, burns, various skin conditions, breakage of bones in delicate areas, and Crohn's disease are just a few examples.

Garment 814, in this example a shirt or T-shirt enabled to be worn by a user surrounding a chest, abdomen and upper arms. A smart fabric bandage or multilayer bandage is formed from multilayer fabric 812. In this embodiment, fabric 812 is surrounding an upper abdomen and lower chest area of a user. Multilayer fabric 812 has an outer layer 810 with microparticles 815 that have opalescent properties. Each layer of the multilayer fabric 812 will comprise elasticity, as discussed above in regards to fabric 10 and 310.

Figure 8B:
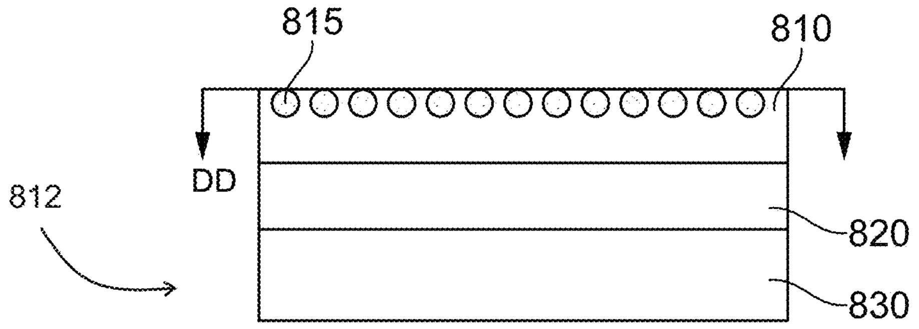
FIG. 8B is a detailed cross-section of the smart fabric of FIG. 8A.

FIG. 8B depicts individual layers of the smart fabric 812 made from tiny spheres or microparticles 815 that are 200 nanometers across, although the particles may be larger or smaller depending on application and type of printer used. In this embodiment, photonic crystal "ink" mimics color-producing structures found in nature. For example, butterfly wings, feathers, and some gemstones derive their shimmering shades from ordered nanostructures that bend and reflect light, rather than from pigments. The shape and arrangement of these tiny nanocrystals determines which colors are produced. Unlike pigments, which look the same from any angle and can bleed and fade, structurally derived colors stay vibrant indefinitely, can appear metallic, and may enigmatically change with viewing angle.

Microparticles 815 are manufactured to copy these properties. Colors and color differentials seen in opals are produced by stacks of tiny silica spheres within the gemstone. Mimicking that arrangement in the lab, using spheres with a hard polystyrene core and softer outer shell, can produce polymer opals. Layering these spheres or microparticles 815 on an elastic fabric, such as the multilayer fabric 10 (FIG. 1) may produce a flexible opal, or material that changes color when twisted, stretched, or bent. As the space between the spheres shrinks and expands, the matrix formed by the applied microparticles 815 diffracts and reflects light of different wavelengths, producing a changing rainbow of colors. The size of the microparticles 815 affects the starting color, with larger spheres appearing red initially, and smaller spheres starting at blue.

Microparticles 815, as shown in an outer elastic layer 810 of the multilayer fabric 812 may be printed into the elastic layer 810, using a printhead that incorporates an electric field. As the microparticles 815 are laid down, varying the voltage affects the spacing between them, which in turn affects the color of that region. The nanoparticles are then fixed into place with UV light.

As discussed, previously, once opalescent microparticles 815 are printed into an elastic layer 810, the top layer of multilayer fabric 812 of FIG. 8B, it may change color when stretched. If one knew a durometer value of elastic layer 810 and the size and beginning color of microparticles 815, printed on elastic layer 810, and a differential caused by the second and third layers 820 and 830 of multilayer fabric 812, one may be able to determine an approximate pressure value applied to tissue under elastic layer 810 merely by viewing the color of the material under a certain light source. The pressure may be given in PSI, Pascals (Pa), Bar (bar), Atmosphere (atm) or millimeters of mercury (mmHg). The multilayer fabric 812 having top layer 810 may be tested prior to packaging and a table included with the material that states a color pressure relationship.

Returning to FIG. 8B, a fabric layer 830, immediately adjacent to tissue, as seen in FIG. 3, may also be made of elastic material having a same durometer value as layer 810. As previously taught in regards to FIG. 3, a first layer 830 of the multilayer fabric 812 is designed to absorb moisture and store the moisture in layer 820. In one embodiment the first layer 830 is a compressive elastic fabric that may be non-stick when making direct contact with wounds of the skin. In embodiments where the multilayer fabric is designed to apply pressure to internal injuries or disease, the first layer 830 and/or second layer 820 may be eliminated. In this embodiment, a manufacturer may produce an entire garment, for example the T-shirt 814 of FIG. 8A, with the multilayer material 812 as shown in FIG. 8A, or just layer 810 having nanoparticles 815.

A specific light source common in medical environments, for example a fluorescent light source, and elastic material or fabric making up layer 810 with known durometer ratings may be used to devise a scale of color related to a range of pressure measured in mmHg, for example. In this example it is also known the beginning size and color of the nanoparticles 815. In this manner a medical professional may know that a burn victim has burns on their abdomen that require being held at a specific pressure. Elastic layer 810 having printed nanoparticles may come out of a package orange-yellow, light stretching to 15-20 mmHg may turn the material green and more stretching to 30-40 mmHg may turn layer 810 blue. The medical professional may merely view a bandage color to know if sufficient pressure is being applied to the tissue for a given disorder, wound or disease.

Figure 9A:
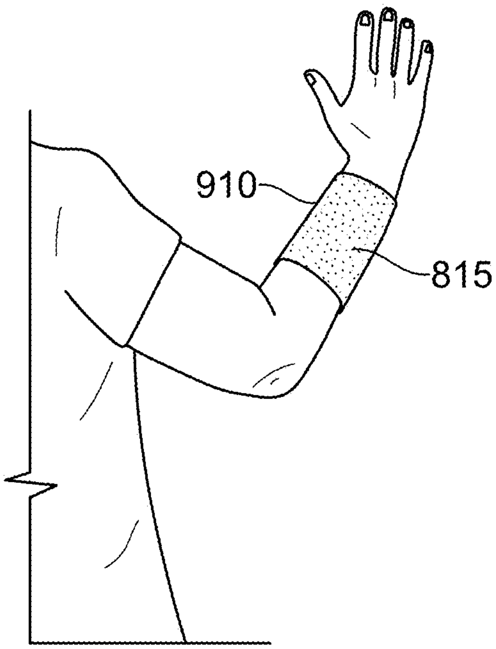
FIG. 9A depicts examples of the smart fabric of FIG. 8A forming an arm band and leg band.
Figure 9B:
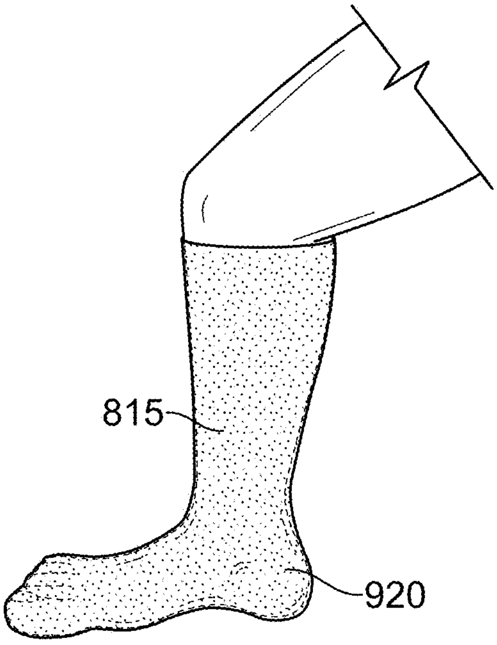
FIG. 9B shown an entire garment created with the smart fabric of FIG. 8A.

FIGS. 9A and 9B depict other versions of bandages 910 and 920 made of material similar to 812 having nanoparticles 815 incorporated as discussed, above. In these embodiments 920 and 910 may be multilayer material as 812 or just a single layer, as 810. Material bandage 910 is shown around an upper arm and material bandage 920 is around a lower leg. FIG. 9B depicts an entire garment in the form of a stocking having a layer or outside layer 930 similar to layer 810 having nanoparticles 815 incorporated, therein.

Figure 10A:
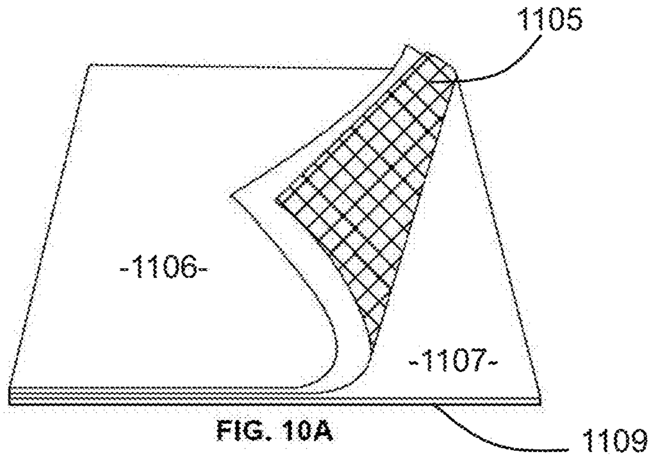
FIG. 10A shows another embodiment of the smart fabric enabled to hold micro sensors.
Figure 10B:
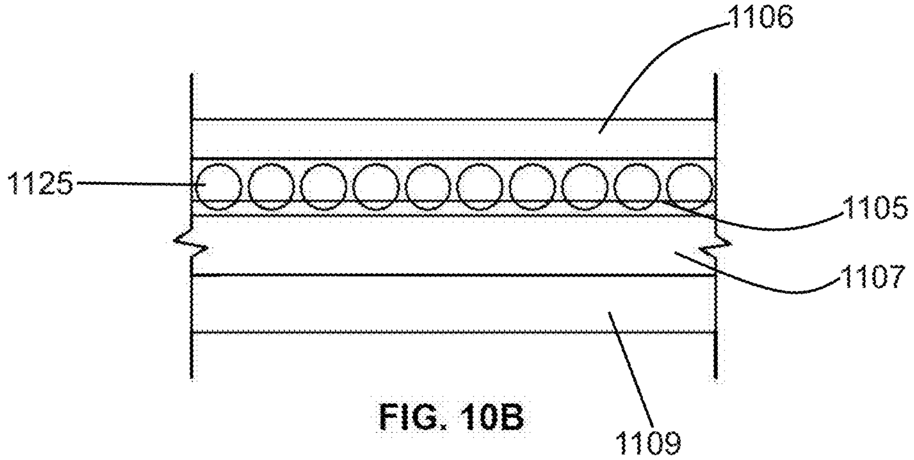
FIG. 10B shows a cross section of the smart fabric of FIG. 10A.
Figure 10C:
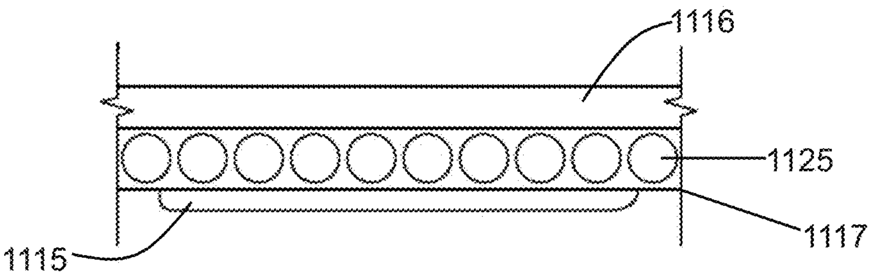
FIG. 10C depicts an elastic top fabric layer which may have conductivity in certain embodiments.

FIG. 10A-10C show an embodiment where a multilayer material 1100 includes microsensor beads 1105 enabled to detect a number of states related to adjacent tissue. In an embodiment depicted in FIG. 10A and 10B pressure may be measured by four elastic layers of different non-conductive and conductive fabrics which ensure good elasticity around the microsensors. Referring to FIG. 10B, the first layer 1106 and the fourth layer 1109 are highly conductive materials including at least silver coated elastic fibers. The material layers 1106 and 1109 are available at different resistances, determined by the thickness of the applied conductive coatings, typically within a range of less than 2 Ω/sq., but may be more or less depending on the state to be measured.

Layer 1107 of FIG. 10B is a force-sensitive resistor layer, or piezoresistive elastic fabric with a volume resistivity of approximately 15-25kΩ·m. Layer 1105 is a mesh fabric layer with a honeycomb arrangement about 0.23 mm thick. Openings formed in the mesh fabric layer 1105_are of a size including ≈2 mm, but may be larger or smaller depending upon application. Microsensor beads 1125 are dispersed within the mesh layer 1105. With this additional mesh layer 1105, the sensor has a very high resistivity. The microsensor beads operate based on the piezoresistive effect, where the electrical resistance of a material changes under mechanical pressure. The sensor uses the mesh layer placed between two highly conductive material layers 1106 and 1107 and there is a change in the resistance measured at the two outer layers when pressure is applied. Sensitivity of microsensor beads 1125 was found to depend on the thickness of the meshed layer and on the size of the mesh openings, with larger openings and thinner layers producing better sensitivity. With the additional mesh layer 1105, the microsensor bead has a very high resistivity when not acted upon, which is achieved by the introduced gap between the electrode and the piezoresistive layer. Due to the minimal force required to close this gap, the sensor is sensitive to subtle forces.

In one embodiment other states of tissue may be discerned with microsensor beads with different capabilities. FIG. 10C depicts an elastic top fabric layer which may have conductivity in certain applications. Microsensor beads 1125 may have direct access to tissue 1115, which may be a wound in this example. In another example, the microsensor beads 1125 may be separated from tissue 1115 by a porous, thin membrane 1117 enabling at least temperature and fluid detection. In this embodiment a mesh layer may be incorporated between layers 1116 and membrane 1117 to retain microsensor beads in place for providing power and signal collection, as discussed below. Microsensor beads 1125 having access to tissue 1115 may be able (with various modifications) to detect pressure, temperature, fluid density, oxygen level, pH level, blood flow, heart rate among other conditions.

In embodiments of the invention, material 1100 may be incorporated as layer 830 in FIG. 8B, for example. In this manner, in a practical example of multilayer bandage 812, pressure may be visible by glancing at the outer layer 810 and other data may be collected with material layer 1100 including temperature, pH and other conditions that may be indicative of tissue infection.

Figure 11:
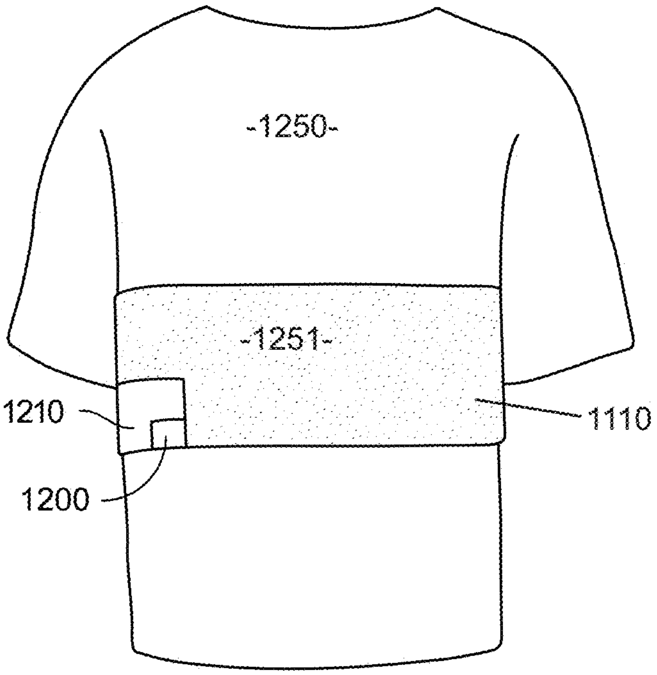
FIG. 11 depicts a garment having the smart fabric enabling electronic communication.

FIG. 11 depicts an embodiment that may be incorporated with embodiments using microsensor beads 1110. Garment 1250, in this embodiment, a T-shirt 1250 includes bandage material layer 1251, which includes at least the microbeads from FIG. 10C. In this embodiment a pouch or pocket 1210 may be integrated in the material 1100. Pocket 1210 may hold a microprocessor 1200 including at least a transceiver capable of short range wireless communication. Microprocessor 1200 is enabled with functionality and software to provide power to at least a conductive layer 1116 or mesh layer 1105 enabling microsensor beads 1110 to be energized and operate to output signals depending on a state or condition of tissue/wound 1115. Mesh material 1105 may communicate signals from microsensor beads 1110 via a connection to graphene traces 1220 providing signal input from microsensor beads 1110 to microprocessor 1200, which may be wirelessly sent to a computerized device, such as an iphone, or other type of device capable of executing software to determine what the received signals may indicate regarding the tissue 1115.

Figure 12:
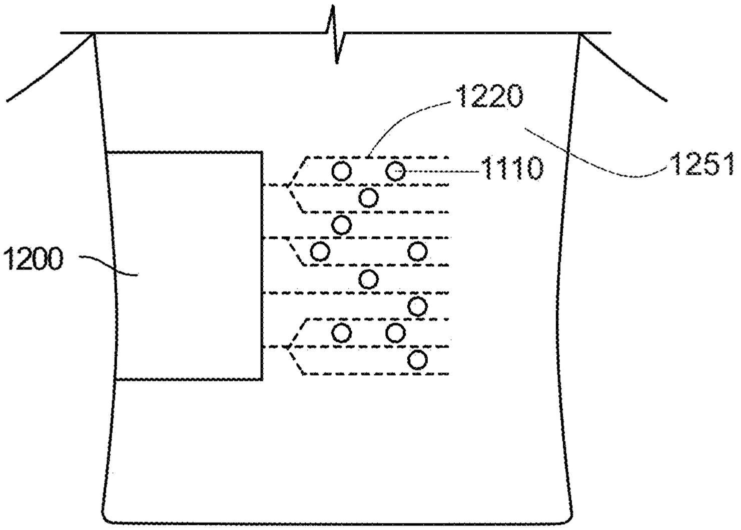
FIG. 12 is a closeup of a processor connected to micro sensors of the smart fabric of FIG. 10A.

FIG. 12 depicts one embodiment enabling signals from microsensor beads 1110 to be input or transferred to microprocessor 1200. In this embodiment signal information, which may be processed by microprocessor 1200 to determine current state of tissue, may be picked up by graphene traces 1220 which may be integrated with mesh material 1105 of FIG. 10. In embodiments that use membrane layer 1117, the graphene layer may be adjacent to the membrane so it may interact with microsensor beads 1125. In either case, the graphene traces are flexible, and may be weaved so elasticity is maintained. Microprocessor 1200 may process signals received from the graphene traces and determine a current state of a wound or tissue and send information via the transceiver via Bluetooth™ or other near field wireless communication. A medical attendant may be notified, or an application on a computerized device may receive the information from the microprocessor and document and alert a medical professional at an outside location via the Internet or cellular network.

Although certain specific embodiments are described above in order to illustrate the invention, the invention is not limited to the specific embodiments. Accordingly, various modifications, adaptations, and combinations of various features of the described embodiments can be practiced without departing from the scope of the invention as set forth in the claims.

What is claimed is:

1. A multilayer fabric comprising:

a third layer, wherein the third layer has a wound or tissue contact surface;

a second layer, wherein the second layer receives and stores tissue moisture, and wherein the tissue moisture is received through the third layer; and a first layer of stretchable fabric;

wherein the first layer has an external environment contact surface including microparticles, the third layer of the multilayer fabric includes microsensor beads incorporated into the contact surface enabled to detect conditions and relay signals to a microprocessor, and wherein the second layer is disposed between the first layer and third layer and the microparticles in the first layer causes changes in color under a light source when stretched and held at a specific pressure range, thereby providing an overall visible color indicating the specific pressure range.

2. The multilayer fabric of claim 1, wherein the first, second and third layers have stretch properties that are consistent with each other so all three layers stretch simultaneously.

3. The multilayer fabric of claim 1, wherein the microparticles have opalescent properties reflecting color under a light source.

4. The multilayer fabric of claim 3, wherein the opalescent properties are provided by colors and color differentials produced by stacks of tiny silica spheres with a hard polystyrene core and softer outer shell.

5. The multilayer fabric of claim 4, wherein the microparticles are layered on the first layer thereby producing a material that changes color when twisted, stretched, or bent as space between the microparticles shrinks and expands which diffracts and reflects light of different wavelengths, producing the colors.

6. The multilayer fabric of claim 1, wherein a size of the microparticles affects the starting color, with larger microparticles appearing red initially, and smaller microparticles starting at blue.

7. The multilayer fabric of claim 1, wherein the microparticles are printed into the first layer using a printhead that incorporates an electric field and wherein varying the voltage affects the spacing between the microparticles, which in turn affects the color of the multilayer fabric when manipulated.

8. The multilayer fabric of claim 7, wherein the microparticles are then fixed into place with UV light.

9. The multilayer fabric of claim 1, wherein a viewable color of the multilayer fabric under a light source and constant pressure range indicates the specific pressure range based upon a calculation of a durometer value of the first layer and a size of the microparticles and a differential caused by durometers of the second and third layers.

10. The multilayer fabric of claim 1, wherein the multilayer fabric is tested prior to packaging determining information including a color and pressure range relationship and the information is included with the packaging.

11. The multilayer fabric of claim 1, wherein the multilayer fabric is formed as a closed loop against the tissue as at least a tubular form.

12. The multilayer fabric of claim 11, wherein the tubular form is incorporated into a stocking.

13. The multilayer fabric of claim 11, wherein the tubular form is formed into a T-shirt.

14. The multilayer fabric of claim 1, wherein the conditions are from a list including at least temperature, fluid density, blood flow, oxygen level and pH.

15. The multilayer fabric of claim 1, wherein a pouch or pocket is integrated within or on the multilayer material enabling containment of the microprocessor including at least a transceiver capable of short-range or near field wireless communication.

16. The multilayer fabric of claim 15, wherein the microprocessor is enabled with functionality and software to provide power to at least a conductive mesh layer incorporated in the third layer making contact with the microsensor beads.

17. The multilayer fabric of claim 16, wherein the conductive mesh layer enables the microsensor beads to be powered up and operate to output signals depending on the condition of the tissue.

18. The multilayer fabric of claim 17, wherein the mesh material includes graphene traces communicating signals from the microsensor beads to the microprocessor.

19. The multilayer fabric of claim 17, wherein the signals are wirelessly sent to a computerized device, such as a smartphone, or other type of computerized device capable of expressing the detected conditions on a display.

* * * * *